(12) United States Patent
Pinkos et al.

(10) Patent No.: US 8,217,186 B2
(45) Date of Patent: Jul. 10, 2012

(54) PROCESS FOR PREPARING EPSILON-CAPROLACTONE

(75) Inventors: Rolf Pinkos, Bad Duerkheim (DE); Gerd-Dieter Tebben, Mannheim (DE); Daniel Breuninger, Bobenheim-Roxheim (DE); Tilman Sirch, Schifferstadt (DE); Christophe Bauduin, Plankstadt (DE); Maria Guixa Guardia, Mannheim (DE); Thomas Krug, Worms (DE)

(73) Assignee: BASF SE, Ludwigshafen (DE)

( * ) Notice: Subject to any disclaimer, the term of this patent is extended or adjusted under 35 U.S.C. 154(b) by 192 days.

(21) Appl. No.: 12/746,680

(22) PCT Filed: Dec. 10, 2008

(86) PCT No.: PCT/EP2008/067180
§ 371 (c)(1),
(2), (4) Date: Jun. 7, 2010

(87) PCT Pub. No.: WO2009/080504
PCT Pub. Date: Jul. 2, 2009

(65) Prior Publication Data
US 2010/0256398 A1  Oct. 7, 2010

(30) Foreign Application Priority Data

Dec. 21, 2007 (EP) .................................... 07150291

(51) Int. Cl.
*C07D 313/00* (2006.01)
(52) U.S. Cl. ...................................................... 549/266
(58) Field of Classification Search .................. 549/266
See application file for complete search history.

(56) References Cited

U.S. PATENT DOCUMENTS

| 5,068,361 A | 11/1991 | Richter et al. |
| 5,981,769 A | 11/1999 | Baur et al. |

FOREIGN PATENT DOCUMENTS

| DE | 1 618 143 | 10/1970 |
| DE | 38 23 213 | 1/1990 |
| DE | 197 50 532 | 5/1999 |
| EP | 0 251 111 | 1/1988 |
| EP | 1 030 827 | 3/2002 |
| WO | 97 31883 | 9/1997 |

OTHER PUBLICATIONS

U.S. Appl. No. 12/952,956, filed Nov. 23, 2010, Pinkos.
U.S. Appl. No. 13/131,130, filed May 26, 2011, Pinkos, et al.
U.S. Appl. No. 13/133,006, filed May 6, 2011, Abillard, et al.
U.S. Appl. No. 13/257,496, filed Sep. 19, 2011, Pinkos, et al.
U.S. Appl. No. 13/258,166, filed Sep. 21, 2011, Pinkos, et al.

*Primary Examiner* — Nizal Chandrakumar
(74) *Attorney, Agent, or Firm* — Oblon, Spivak, McClelland, Maier & Neustadt, L.L.P.

(57) ABSTRACT

The invention relates to a process for preparing ε-caprolactone from 6-hydroxycaproic ester in the gas phase in the presence of activated carbon as a catalyst and subsequent distillation.

15 Claims, 1 Drawing Sheet

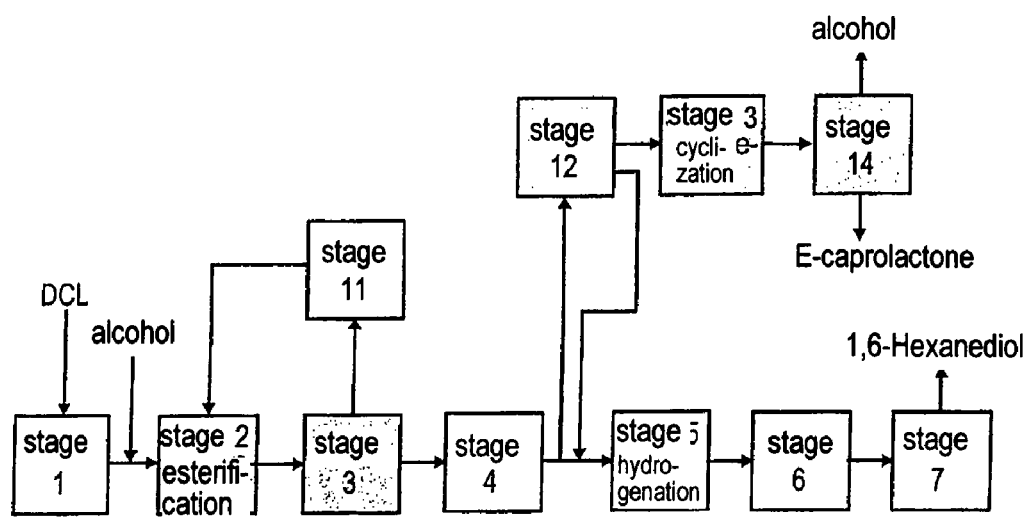

PROCESS FOR PREPARING EPSILON-CAPROLACTONE

The invention relates to a process for preparing ε-caprolactone from 6-hydroxycaproic ester in the gas phase in the presence of activated carbon as a catalyst and subsequent distillation.

ε-Caprolactone or the polycaprolactones prepared therefrom by polyaddition serve to prepare polyurethanes.

The aqueous solutions of carboxylic acids, which are formed as by-products in the oxidation of cyclohexane to cyclohexanol and cyclohexanone, as described in Ullmann's Encyclopedia of Industrial Chemistry, 5th ed., 1987, Vol. A8, page 49, referred to hereinafter as dicarboxylic acid solution (DCS), comprise (calculated neglecting water in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cyclohexanediols, between 1 and 5% 1,4-cyclohexanediols, between 2 and 10% formic acid, and a multitude of further mono- and dicarboxylic acids, ester, oxo and oxa compounds, whose individual contents generally do not exceed 5%. Examples include acetic acid, propionic acid, butyric acid, valeric acid, caproic acid, oxalic acid, malonic acid, succinic acid, 4-hydroxybutyric acid and gamma-butyrolactone.

The preparation of caprolactone from DCS has also already been described, for example, from DE 1 618 143. In this method, dewatered DCS is reacted thermally with phosphoric acid and a mixture of dicarboxylic acids, caprolactone and a multitude of other components is fractionated. The bottoms are in some cases obtained in solid and sparingly soluble form. However, the caprolactone still has only 98% purity even after further distillative workup.

Furthermore, DE 38 23 213 describes the conversion of 6-hydroxycaproic esters to caprolactone in the gas phase in the presence of oxidic catalysts and of an inert carrier gas. A disadvantage compared to the process according to the invention is the use of oxidic catalysts in the gas phase, since they tend to form by-products to an enhanced degree.

Moreover, WO 97/31883 describes a process for preparing 1,6-hexanediol and ε-caprolactone from a carboxylic acid mixture which comprises adipic acid, 6-hydroxy-caproic acid and small amounts of 1,4-cyclohexanediols and is obtained as a by-product of the oxidation of cyclohexane to cyclohexanone/cyclohexanol with oxygen or oxygen-comprising gases and by water extraction of the reaction mixture, and this mixture is esterified with a low molecular weight alcohol to give the corresponding carboxylic esters, the resulting esterification mixture is freed of excess alcohol and low boilers in a first distillation stage, the bottom product is separated in a second distillation stage into an ester fraction essentially free of 1,4-cyclohexanediols and a fraction comprising at least the majority of the cyclohexanediols, obtaining a fraction comprising essentially 6-hydroxycaproic acid (stage 12) by means of a third distillation stage and cyclizing it to ε-caprolactone in the gas or liquid phase.

Since there is barely any difference between the boiling range of adipic ester and 6-hydroxycaproic ester, it is generally possible to obtain the two substances without the other in each case only with an extremely high level of distillation complexity, for example by using columns with a very high number of plates and a correspondingly high energy expenditure, or by adding an extraneous substance which has a boiling point between the two esters.

In order to reduce the separation complexity and in order to obtain pure 6-hydroxy-caproic ester, the distillative separation of the two $C_6$ esters in the third distillation stage, according to WO 97/31883, has to date been carried out in such a way that the adipic ester to be hydrogenated to 1,6-hexanediol still comprised from 0.2 to 7% by weight of 6-hydroxycaproic ester based on the content of 6-hydroxycaproic ester which goes into the hydrogenation to 1,6-hexanediol together with adipic ester. In the case of a high demand for 1,6-hexanediol, with a further reduction in the separation complexity, it is also possible to remove even more 6-hydroxycaproic ester together with adipic ester and to hydrogenate it to 1,6-hexanediol. The 6-hydroxycaproic ester content of the dicarboxylic acid solution has therefore never been utilized completely for caprolactone preparation to date.

When the utilization of more than 50%, preferably >80%, more preferably >90%, of the content of 6-hydroxycaproic ester for caprolactone preparation is desired, without an extremely high level of distillation complexity or the addition of an extraneous substance, the cyclization of the 6-hydroxycaproic ester stream has to be possible without disadvantages in the presence of adipic ester in amounts of at least 0.5% by weight, generally from >1% up to 25% by weight, based on the overall feed to the caprolactone synthesis.

WO 97/31883 recommends the preparation of caprolactone in the liquid phase. According to comparative example 1 present in this application, for the cyclization in the liquid phase in the presence of 5% by weight of adipic ester, based on the 6-hydroxycaproic ester, however, a significant decline in the yield of caprolactone is observed.

This decline in yield is attributable to polymerization side reactions in the ε-caprolactone cyclization. In the presence of catalysts, adipic esters and 6-hydroxycaproic esters can form dimers, oligomers or polymers. Dimethyl adipate and methyl 6-hydroxycaproate can form, for example, the dimeric ester $CH_3OOC-(CH_2)_4-COO-(CH_2)_5-COOCH_3$ which can form oligomers or polymers with incorporation of further 6-hydroxycaproic esters. Although these dimers, oligomers or polymers still constitute compounds utilizable by hydrogenation for 1,6-hexanediol, the risk of deposits of these high-boiling components on the cyclization catalyst in the case of reactions in the gas phase is high, and so a very shortened catalyst lifetime would have to be expected.

Moreover, it was known from EP-A 251 111 that adipic esters are converted in the presence of catalysts to cyclopentanones and are thus no longer available for other applications, for example the conversion to 1,6-hexanediol.

It was therefore an object of the invention to provide a process for preparing caprolactone in a purity of more than 99% proceeding from 6-hydroxycaproic esters or mixtures thereof with adipic esters, in which a reduction in the separation complexity and the utilization of more than 50%, preferably >80%, more preferably >90%, of the content of 6-hydroxycaproic ester for caprolactone preparation are combined and, through avoidance of polymerization side reactions in the ε-caprolactone cyclization, good catalyst lifetimes and caprolactone yields and selectivities are achieved. In addition, a minimum amount of adipic ester should be converted, since it should as far as possible still be available to other applications after removal of caprolactone.

This object is achieved by a process for preparing ε-caprolactone in a purity of more than 99%, which comprises cyclizing 6-hydroxycaproic ester comprising from 0 to 40% by weight of adipic ester in the gas phase at from 150 to 450° C. in the presence of activated carbon as a catalyst, and obtaining 6-caprolactone from the cyclization product by distillation.

The process according to the invention is advantageous when the 6-hydroxycaproic acid comprises from 0.5 to 40% by weight of adipic ester.

The process according to the invention is advantageous when the 6-hydroxycaproic ester comprising from 0 to 40% by weight of adipic ester is obtained by catalytic hydrogenation of adipic esters or reactant streams which comprise these esters as significant constituents, distillation of the hydrogenation effluent and removal of the hexanediol.

The process according to the invention is advantageous when a carboxylic acid mixture which comprises adipic acid, 6-hydroxycaproic acid and up to 5% by weight of 1,4-cyclohexanediols and is obtainable as a by-product of the oxidation of cyclohexane to cyclohexanone/cyclohexanol with oxygen or oxygen-comprising gases by water extraction of the reaction mixture is esterified with an alcohol which comprises from 1 to 12 carbon atoms to give the corresponding carboxylic esters, and the esterification mixture thus obtained is separated in at least one distillation stage so as to obtain the 6-hydroxycaproic ester stream comprising from 0 to 40% by weight of adipic ester.

The process according to the invention is advantageous when methyl 6-hydroxy-caproate comprising from 0 to 40% by weight of dimethyl adipate is prepared by
  freeing the resulting esterification mixture of excess methanol and low boilers in a first distillation stage,
  in a second distillation stage, separating the bottom product into an ester fraction having a content of less than 20% 1,4-cyclohexanediols based on the original content of 1,4-cyclohexanediols in the ester mixture and a fraction comprising more than 80% 1,4-cyclohexanediols based on the original content of 1,4-cyclohexanediols in the ester mixture,
  in a third distillation stage, removing the methyl 6-hydroxycaproate stream comprising from 0 to 40% by weight of dimethyl adipate from the ester fraction.

The process according to the invention is advantageous when cyclization is effected in the presence of an inert carrier gas selected from nitrogen, carbon dioxide, hydrogen and noble gases.

The process according to the invention is advantageous when cyclization is effected at from 150 to 450° C.

The 6-hydroxycaproic ester used in the process according to the invention comprises from 0 to 40% by weight, preferably from 0.5 to 25% by weight, more preferably from 0.6 to 15% by weight, of adipic ester and is cyclized to $\epsilon$-caprolactone in the gas phase at from 150 to 450° C. in the presence of activated carbon as a catalyst and the $\epsilon$-caprolactone is subsequently obtained from the cyclization product by distillation.

The alcohols of the 6-hydroxycaproic ester and of the adipic ester used for the esterification are generally alkanols having from 1 to 12 carbon atoms, cycloalkanols having from 5 to 7 carbon atoms, aralkanols having from 7 to 8 carbon atoms or phenols having from 6 to 8 carbon atoms. It is possible to use methanol, ethanol, propanol, isopropanol, n- or i-butanol or else n- or i-pentanol, or mixtures of the alcohols, but preferably alcohols having from 1 to 4 carbon atoms, more preferably methanol. Diols such as butanediol or pentanediol are also useful in principle. The ester groups in the 6-hydroxycaproic esters and the adipic esters may be the same or different, but they are preferably the same. The particularly preferred reactant is methyl 6-hydroxycaproate comprising from 0 to 40% by weight of dimethyl adipate.

The reactant of the process according to the invention, the 6-hydroxycaproic ester comprising from 0 to 40% by weight of adipic ester, can also be prepared according to DE-A 197 50 532, which is hereby explicitly incorporated by reference.

According to DE-A 197 50 532, 6-hydroxycaproic ester comprising from 0 to 40% by weight of adipic ester is obtained by catalytic hydrogenation of adipic esters or reactant streams which comprise these esters as essential constituents, distillation of the hydrogenation effluent and removal of the hexanediol.

The hydrogenation is preferably carried out in the liquid phase. The hydrogenation catalysts used in this process are generally heterogeneous, but also homogeneous, catalysts suitable for hydrogenating carbonyl groups. They may be used either in fixed bed form or mobile form, for example in a fluidized bed reactor. Examples thereof are described, for example, in Houben-Weyl, Methoden der Organischen Chemie [Methods of organic chemistry], Volume IV/1c, p. 16 to 26.

Among the hydrogenation catalysts to be used, preference is given to those which comprise one or more elements from group Ib, VIb, VIIb and VIIIb, and also IIIa, IVa and Va, of the Periodic Table of the Elements, especially copper, chromium, rhenium, cobalt, rhodium, nickel, palladium, iron, platinum, indium, tin and/or antimony. Particular preference is given to catalysts which comprise copper, cobalt and/or rhenium.

In addition, the 6-hydroxycaproic ester comprising from 0 to 40% by weight of adipic ester can be prepared according to WO 97/31 883, which is hereby incorporated by reference.

The 6-hydroxycaproic ester comprising from 0 to 40% by weight of adipic ester is prepared according to WO 97/31 883 by esterifying a carboxylic acid mixture which comprises adipic acid, 6-hydroxycaproic acid and small amounts of 1,4-cyclohexane-diols and is obtainable as a by-product of the oxidation of cyclohexane to cyclohexanone/cyclohexanol with oxygen or oxygen-comprising gases by water extraction of the reaction mixture with a low molecular weight alcohol to give the corresponding carboxylic esters, and separating the esterification mixture thus obtained in at least one distillation stage.

In a preferred embodiment, methyl 6-hydroxycaproate comprising from 0 to 40% by weight of dimethyl adipate is obtained by
  freeing the resulting esterification mixture of excess methanol and low boilers in a first distillation stage,
  in a second distillation stage, separating the bottom product into an ester fraction having a content of less than 20% 1,4-cyclohexanediols based on the original content of 1,4-cyclohexanediols in the ester mixture and a fraction comprising more than 80% 1,4-cyclohexanediols based on the original content of 1,4-cyclohexanediols in the ester mixture,
  in a third distillation stage, removing the methyl 6-hydroxycaproate stream comprising from 0 to 40% by weight of dimethyl adipate from the ester fraction.

For better understanding, the process for preparing $\epsilon$-caprolactone according to WO 97/31883 is illustrated in FIG. 1, in which the individual process steps are broken down into further stages, of which stages 2, 3, 4 and 12, 13 and 14 are essential for the process for preparing $\epsilon$-caprolactone and stages 3 and 4 can also be combined.

The dicarboxylic acid solution (DCS) is generally an aqueous solution having a water content of from 20 to 80% by weight. Since an esterification reaction is an equilibrium reaction in which water is formed, it is advisable to remove water present before the reaction, especially in the case of esterification with, for example, methanol, in particular when water cannot be removed, for example cannot be removed azeotropically, during the esterification reaction. The dewatering in stage 1 can be effected, for example, with a membrane system, or preferably by means of a distillation apparatus in which water is removed via the top and $C_3$-$C_7$-monocarboxylic acids, dicarboxylic acids and 1,4-cyclohexanediols are removed via the bottom at from 10 to 250° C., preferably from 20 to 200° C., more preferably from 30 to 200° C., and a pressure of from 1 to 1500 mbar, preferably from 5 to 1100 mbar, more preferably from 20 to 1000 mbar. The bottom temperature is preferably selected such that the bottom product can be drawn off in liquid form. The water content in the bottom of the column may be from 0.01 to 10% by weight, preferably from 0.01 to 5% by weight, more preferably from 0.01 to 1% by weight.

The water can be removed in such a way that the water comprises a carboxylic acid content of <0.5% by weight, or the $C_1$-$C_3$-monocarboxylic acids present in the DCS—with a formic acid of >60% by weight in these carboxylic acids—can be distilled off with the water to an extent of >80%, in order that they do not bind any esterification alcohol in the esterification.

Alcohol ROH having from 1 to 10 carbon atoms is added to the carboxylic esters from stage 1. It is possible to use methanol, ethanol, propanol or isopropanol or mixtures of the alcohols, but preferably either methanol or $C_4$ and higher alcohols, especially having from 4 to 8 carbon atoms and preferably n- or i-butanol or else n-pentanol or i-pentanol. The mixing ratio of alcohol to carboxylic acid stream (mass ratio) may be from 0.1 to 30, preferably from 0.2 to 20, more preferably from 0.5 to 10.

This mixture passes as a melt or solution into the reactor of stage 2, in which the carboxylic acids are esterified with the alcohol. The esterification reaction can be carried out at from 50 to 400° C., preferably from 70 to 300° C., more preferably from 90 to 200° C. It is possible to apply an external pressure, but preference is given to performing the esterification under the autogenous pressure of the reaction system. The esterification apparatus used may be a stirred tank or flow tube, or it is possible to use more than one of each. The residence time needed for the esterification is between 0.3 and 10 hours, preferably from 0.5 to 5 hours. The esterification reaction can proceed without addition of a catalyst, but preference is given to increasing the reaction rate by adding a catalyst. This may be a homogeneous dissolved catalyst or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium, boron compounds. Preference is given to mineral acids, especially sulfuric acid. The weight ratio of homogeneous catalyst to carboxylic acid melt is generally from 0.0001 to 0.5, preferably from 0.001 to 0.3.

Suitable solid catalysts are acidic or superacidic materials, for example acidic and superacidic metal oxides such as $SiO_2$, $Al_2O_3$, $SnO_2$, $ZrO_2$, sheet silicates or zeolites, all of which may be doped with mineral acid residues such as sulfate or phosphate to increase the acid strength, or organic ion exchangers with sulfonic acid or carboxylic acid groups. The solid catalysts may be arranged as a fixed bed or used as a suspension.

The water formed in the reaction is appropriately removed continuously, for example by a membrane, or by distillation.

The completeness of the conversion of the free carboxyl groups present in the carboxylic acid melt is determined by the acid number measured after the reaction (mg KOH/g). Minus any acid added as a catalyst, it is from 0.01 to 50, preferably from 0.1 to 10. Not all carboxyl groups present in the system need be present as the ester of the alcohol used, but rather a portion may be present in the form of dimeric or oligomeric esters with the OH end of the hydroxycaproic acid.

The esterification mixture is fed into stage 3, a membrane system or preferably a distillation column. When a dissolved acid has been used as a catalyst for the esterification reaction, the esterification mixture is appropriately neutralized with a base, from 1 to 1.5 base equivalents being added per acid equivalent of the catalyst.

The bases used are generally alkali metal or alkaline earth metal oxides, alkali metal or alkaline earth metal carbonates, alkali metal or alkaline earth metal hydroxides or alkali metal or alkaline earth metal alkoxides, or amines in substance or dissolved in the esterification alcohol. However, it is also possible to neutralize with basic ion exchangers.

When a column is used in stage 3, the feed to the column is preferably between the top stream and the bottom stream. Drawn off via the top at pressures of from 1 to 1500 mbar, preferably from 20 to 1000 mbar, more preferably from 40 to 800 mbar, and temperatures between 0 and 150° C., preferably 15 and 90° C. and especially 25 and 75° C., are the excess esterification alcohol ROH, water and corresponding esters of formic acid, acetic acid and propionic acid. This stream can either be incinerated or preferably worked up further in stage 11.

The bottoms obtained are an ester mixture which consists predominantly of the esters of the alcohol ROH used with dicarboxylic acids such as adipic acid and glutaric acid, hydroxycarboxylic acids such as 6-hydroxycaproic acid and 5-hydroxyvaleric acid, and also of oligomers and free or esterified 1,4-cyclohexanediols. It may be advisable to permit a residual content of water and/or alcohol ROH of up to 4% by weight each in the ester mixture. The bottom temperatures are from 70 to 250° C., preferably from 80 to 220° C., more preferably from 100 to 190° C.

The stream from stage 3, which comprises a residual content of water and esterification alcohol ROH of in each case below 5% by weight, is fed into stage 4. The column is operated at temperatures of from 10 to 300° C., preferably from 20 to 270° C. and more preferably from 30 to 250° C., and pressures of from 1 to 1000 mbar, preferably from 5 to 500 mbar and more preferably from 10 to 200 mbar. The top fraction comprises up to 100% by weight of residual water and residual alcohol ROH, esters of the alcohol ROH with monocarboxylic acids, predominantly $C_3$- to $C_6$-monocarboxylic esters with hydroxycarboxylic acids, such as 6-hydroxycaproic acid, 5-hydroxyvaleric acid, and in particular the diesters with dicarboxylic acids such as adipic acid, glutaric acid and succinic acid, cyclohexanediols, caprolactone and valerolactone.

The components mentioned can be removed together via the top or, in a further preferred embodiment, can be separated in the stage 4 column into a top stream, which comprises up to 99% by weight of residual water and residual alcohol and the abovementioned constituents having from 3 to 5 carbon atoms, and a side stream, which comprises up to 99% by weight of the abovementioned constituents of the $C_6$ esters. The stream comprising the esters of the $C_6$ acids, either as an overall top stream or as a side stream, can then, depending on how much caprolactone is to be prepared, be fed into stage 12 only partly or as a complete stream as per the process preferred according to WO 97/31883.

The high-boiling components, i.e. those which have a boiling point equal to or higher than the 1,4-cyclohexanediols of the stream from stage 4, comprising dimeric or oligomeric esters, cyclohexanediols and constituents of the DCS which are not defined in more detail and some of which are polymeric, are removed via the stripping section of the column of stage 4. They can either be incinerated or, in a preferred embodiment, pass into the stage 8 described in WO 97/31883 for transesterification.

Stages 3 and 4 can be combined, especially when only relatively small amounts are processed. Stages 3, and 4 are preferably lived together when less than 100 t are prepared per year. To this end, for example, the $C_6$ ester stream can be obtained in a batchwise fractional distillation.

For the caprolactone preparation, the stream comprising up to 99% by weight of esters of the $C_6$ acids from stage 4 is used. To this end, this stream is separated in stage 12, a distillation column, into a stream comprising up to 98% by weight of adipic ester via the top and a stream comprising predominantly 6-hydroxycaproic ester via the bottom. The column is operated at pressures of from 1 to 500 mbar, preferably from 5 to 350 mbar, more preferably from 10 to 200 mbar, and bottom temperatures of from 80 to 250° C., preferably from 100 to 200° C., more preferably from 110 to 180° C. The top temperatures are established correspondingly.

What is important for a high purity and high yield of caprolactone is the removal of the 1,2-cyclohexanediols from the hydroxycaproic ester, since these components form azeotropes with one another. It was not foreseeable in this stage 12 that the separation of the 1,2-cyclohexanediols and of the hydroxycaproic ester succeeds completely, in particular when the ester used is the preferred methyl ester.

It may be advantageous also to remove a little hydroxycaproic ester together with the adipic ester in stage 12. When the adipic ester is to be hydrogenated to 1,6-hexanediol, the contents in the adipic ester of hydroxycaproic ester are advantageously between 0.2 and 20% by weight. According to the alcohol component of the ester, this proportion of hydroxycaproic ester is removed with the adipic ester via the top (e.g. methyl ester) or via the bottom (e.g. butyl ester).

The stream comprising 6-hydroxycaproic ester which comprises from 0 to 40% by weight of adipic ester is converted to alcohol and caprolactone in the gas phase. These mixtures of 6-hydroxycaproic esters and adipic esters may also comprise further components which may make up a proportion by weight of up to 20%, but are preferably below a content of 10%, more preferably below 5%. These components are, for example, 1,5-pentanediol, cyclohexanediols, unsaturated adipic esters, pimelic esters, caprolactone, 5-hydroxycaproic esters and diesters based, in particular, on 6-hydroxycaproic esters.

The evaporation is effected at from 180 to 300° C. It may be advantageous to additionally evaporate a solvent inert under the reaction conditions. Useful solvents of this type include, for example, ethers such as tetrahydrofuran or dioxane, but also alcohols. It is advantageous to use from 10 to 95% by weight solutions of 6-hydroxy-caproic esters and adipic esters in such solvents as the reactant for the process according to the invention.

Inert carrier gases are, for example, nitrogen, carbon dioxide, hydrogen or noble gases, for example argon. Preference is given to using nitrogen or hydrogen as the carrier gas. In general, from 5 to 100 mol of carrier gas, preferably from 8 to 50 mol, more preferably from 10 to 30 mol, are used per mole of vaporous 6-hydroxycaproic ester. The carrier gas is preferably circulated by means of a blower or of a compressor, and a substream can be discharged and replaced correspondingly by fresh gas.

Suitable catalysts for the preparation of caprolactone by cyclization of 6-hydroxycaproic esters are activated carbons. Activated carbons are understood to mean carbon-comprising materials which can be produced, for example, proceeding from wood, sawdust, coconut shells or brown coal, by chemical or physical activation processes (Ullmann's Encyclopedia of Industrial Chemistry, 6th Edition, Volume 6, pages 326 to 350).

Activated carbons are porous, possess a high surface area and consist of very small crystals with graphite structure. The interstices between the crystals consist of amorphous carbon.

For the preparation of caprolactone, activated carbons in the form of powders, granules or, more preferably, of shaped bodies are suitable. Their internal surface area is greater than 400 m$^2$/g and is generally from 500 m$^2$/g to 1500 m$^2$/g. The branched pore system comprises mesopores (d=from 2 to 50 nm), micropores (d=from 0.8 to 2 nm), submicropores (d$\leqq$0.8 nm) and macropores (d$\geqq$50 nm).

The pore volume for the process according to the invention is greater than 25 cm$^3$/100 g.

On the surface of the activated carbon, functional groups, for example carbonyl, carboxyl or phenol groups, may be present, which have originated from the starting compounds of the activated carbons or have formed in the activation processes.

The mixtures of 6-hydroxycaproic esters and from 0 to 40% of adipic esters in the presence of activated carbon as a catalyst can be cyclized in the liquid phase, but preferably the gas phase.

The activated carbons mentioned may also serve as support substances for the following metal oxides: magnesium oxide, zinc oxide, boron trioxide, titanium dioxide, silicon dioxide, tin dioxide, bismuth oxide, copper oxide, lanthanum oxide, zirconium dioxide, vanadium oxides, chromium oxides, tungsten oxides, iron oxides, cerium oxide, aluminum oxide, hafnium oxide, lead oxide, antimony oxide, barium oxide, calcium oxide, sodium hydroxide, potassium hydroxide and neodymium oxide, which are suitable as catalysts for the cyclization of mixtures of 6-hydroxycaproic esters and adipic esters.

The activated carbon catalysts may be arranged in fixed bed form in the reaction zone and the vaporous mixture of 6-hydroxycaproic esters, from 0 to 40% by weight of adipic esters and carrier gases can be passed over them. However, it is also possible that the catalyst is present in upward and downward motion (fluidized bed). Advantageously, a catalyst loading of from 0.01 to 40 g, preferably from 0.05 to 20 g and especially from 0.07 to 10 g of reactant (mixture of 6-hydroxycaproic ester and if appropriate adipic ester) per g of catalyst and hour is maintained.

The cyclization reaction can also be conducted in the absence of a cyclization catalyst. For the reaction, however, higher temperatures or longer residence times in the reactor are then required than in the process according to the invention.

The inventive conversion to caprolactone is carried out at a temperature of from 150 to 450° C., preferably at from 200 to 400° C., especially from 230 to 350° C. In general, the reaction is carried out under atmospheric pressure. However, it is also possible to employ slightly reduced pressure, for example up to 500 mbar, or slightly elevated pressure, for example up to 5 bar. When a fixed bed catalyst is used, it has been found to be particularly favorable that a higher pressure is established upstream of the catalyst than downstream of the catalyst, such that any high-boiling components which form can be deposited on the catalyst to a lesser extent, if at all.

The reaction effluent is condensed with suitable cooling apparatus. When a fixed bed catalyst is used, the reactor, for example a shaft reactor or a tube bundle reactor, can be operated in upward or downward flow mode. The reaction is effected in at least one reactor.

The reaction effluent of the cyclization comprises, as the main component, the target product caprolactone, and also the $C_1$-$C_6$-alcohol released in the cyclization, if appropriate adipic ester and if appropriate unconverted 6-hydroxycaproic ester, if appropriate oligoester and if appropriate solvent. This mixture is separated by a single-stage or multistage distillation in stage 14 under reduced pressure, such that caprolactone is obtained in a purity of at least 99%. The purity is preferably more than 99.5%, more preferably more than 99.8%.

The single-stage or multistage distillations to purify the caprolactone are carried out at bottom temperatures of from 70 to 250° C., preferably from 90 to 230° C., more preferably from 100 to 210° C., and pressures of from 1 to 500 mbar, preferably from 5 to 200 mbar, more preferably from 10 to 150 mbar.

When a column is used for this purpose, any esterification alcohol still present and other $C_1$ to $C_6$ low boilers are removed via the top, pure caprolactone via the side stream, and adipic ester and any as yet unconverted hydroxycaproic ester, which is recycled, via the bottom. The adipic ester can, if appropriate together with dimeric or oligomeric esters, be introduced into a hydrogenation reactor and converted to 1,6-hexanediol according to WO 97/31883 or DE-A-19750532. When methanol has been used as the esterification alcohol, the azeotrope of dimethyl adipate and caprolactone may also be obtained via the top, which can either pass into the hydrogenation to 1,6-hexanediol or be recycled into the process, for example into the stages after the esterification.

When unconverted 6-hydroxycaproic ester is obtained, it is preferably passed into the distillative ester separation upstream of the caprolactone synthesis stage for recovery. In principle, it is of course also possible to conduct it together with the adipic esters into the hydrogenation to 1,6-hexanediol.

If oligomeric $C_6$ esters are formed, they can, according to EP-B 1 030 827, likewise be introduced into the hydrogenation to 1,6-hexanediol.

The process according to the invention for preparing caprolactone in a purity of more than 99% by cyclization of mixtures of 6-hydroxycaproic esters and from 0 to 40% by weight of adipic esters in the presence of activated carbon as a catalyst or without catalyst can be carried out with long catalyst lifetimes. High ester conversions are combined with achievement of high caprolactone selectivities.

The process will be illustrated in detail with reference to the examples which follow, but is in no way restricted thereby.

EXAMPLE 1

A methyl 6-hydroxycaproate stream, which comprised 84.0% methyl 6-hydroxy-caproate, 1.6% 1,4-cyclohexanediols, 1.4% 1,5-pentanediol, 5.0% unsaturated dimethyl adipate, 2.8% dimethyl adipate, 0.2% dimethyl pimelate, 1.6% dimeric esters and further compounds whose amounts were each below 0.1%, prepared according to WO 97/31.883, was pumped into an evaporator at 280° C. and passed from there in gaseous form, together with approx. 800 l (STP) of hydrogen/h at 280° C. and standard pressure over 3000 ml of Supersorbon K (from DonauCarbon, 4 mm extrudates). The reaction effluent was condensed by means of a water cooler and analyzed. The catalyst loading at various experiment settings was between 0.05 and 0.09 kg of feed/liter of catalyst*h. Overall, the experiment was conducted over a period of 14 days. The hydroxycaproic ester conversions were from approx. 95 to 97% and caprolactone yields between 96 and 98%. As a further product, dimeric caprolactone was found with 2-3% yield (in principle, it was possible to recycle this into the reaction in order to increase the yield). Both the saturated and the unsaturated dimethyl adipate passed through the catalyst virtually unchanged.

The collected reaction effluents were distilled batchwise in a 1 m column with random packing. At 10 mbar, caprolactone was obtainable in a purity of up to 99.8%.

The invention claimed is:

1. A process for preparing ε-caprolactone in a purity of more than 99%, comprising:
   cyclizing 6-hydroxycaproic ester comprising from 0 to 40% by weight of adipic ester in gas phase at from 150 to 450° C. in the presence of activated carbon as a catalyst to obtain a cyclization product; and
   distilling the cyclization product to obtain ε-caprolactone.

2. The process according to claim 1, wherein the 6-hydroxycaproic comprises from 0.5 to 40% by weight of adipic ester.

3. The process according to claim 1, wherein the 6-hydroxycaproic ester comprising from 0 to 40% by weight of adipic ester is obtained by catalytic hydrogenation of adipic esters or reactant streams which comprise said adipic esters as significant constituents to obtain a hydrogenation effluent, distillation of the hydrogenation effluent, and removal of hexanediol.

4. The process according to claim 1, wherein a carboxylic acid mixture which comprises adipic acid, 6-hydroxycaproic acid, and up to 5% by weight of 1,4-cyclohexanediols, said carboxylic acid mixture obtained as a by-product of an oxidation of cyclohexane to cyclohexanone/cyclohexanol with oxygen or at least one oxygen-comprising gas, yielding a reaction mixture, by water extraction of the reaction mixture, is esterified esterification of the reaction mixture with an alcohol which comprises from 1 to 12 carbon atoms to give at least one corresponding carboxylic ester in an esterification mixture, and separation of the esterification mixture by at least one distillation to obtain a 6-hydroxycaproic ester stream comprising from 0 to 40% by weight of adipic ester.

5. The process according to claim 1, wherein methyl 6-hydroxycaproate comprising from 0 to 40% by weight of dimethyl adipate is prepared by a process comprising:
   freeing an esterification mixture of excess methanol and low boilers by a first distillation, leaving a bottom product,
   separating the bottom product into an ester fraction comprising less than 20% 1,4-cyclohexanediols based on the original content of 1,4-cyclohexanediols in the esterification mixture, and a fraction comprising more than 80% 1,4-cyclohexanediols based on the original content of 1,4-cyclohexanediols in the esterification mixture, by a second distillation; and
   removing a methyl 6-hydroxycaproate stream comprising from 0 to 40% by weight of dimethyl adipate from the ester fraction by a third distillation.

6. The process according to claim 1, wherein cyclization is effected in the presence of an inert carrier gas selected from the group consisting of nitrogen, carbon dioxide, hydrogen and a noble gas.

7. The process according to claim 1, wherein the cyclizing is effected at from 150 to 450° C. 200 to 400° C.

8. The process according to claim 1, wherein the cyclizing is effected at from 230 to 350° C.

9. The process according to claim 1, wherein the distilling is effected at a bottom column temperature of from 70 to 250° C.

10. The process according to claim 1, wherein the distilling is effected at a bottom column temperature of from 90 to 230° C.

11. The process according to claim 1, wherein the distilling is effected at a bottom column temperature of from 100 to 210° C.

12. The process according to claim 1, wherein the distilling is effected at a pressure of from 1 to 500 mbar.

13. The process according to claim 1, wherein the distilling is effected at a pressure of from 5 to 200 mbar.

14. The process according to claim 1, wherein the distilling is effected at a pressure of from 10 to 150 mbar.

15. The process according to claim 4, wherein the alcohol is at least one selected from the group consisting of methanol, ethanol, propanol, isopropanol, n- or i-butanol, and n- or i-pentanol.

* * * * *